United States Patent [19]
Layman et al.

[11] Patent Number: 5,658,709
[45] Date of Patent: *Aug. 19, 1997

[54] METHOD FOR MANUFACTURING IMPLANTABLE CARDIAC DEFIBRILLATION ELECTRODES USING A LASER BEAM MATERIAL REMOVAL PROCESS

[75] Inventors: Ted W. Layman, Cupertino; Michael L. Reo, San Jose, both of Calif.

[73] Assignee: Ventritex, Inc., Sunnyvale, Calif.

[*] Notice: The term of this patent shall not extend beyond the expiration date of Pat. No. 5,580,699.

[21] Appl. No.: 552,765

[22] Filed: Nov. 3, 1995

Related U.S. Application Data

[63] Continuation of Ser. No. 291,259, Aug. 16, 1994, Pat. No. 5,580,699.

[51] Int. Cl.⁶ .................................................. G03F 7/26
[52] U.S. Cl. ........................ 430/311; 430/319; 430/329; 430/945; 216/65
[58] Field of Search ............................ 430/311, 313, 430/315, 319, 327, 329, 945; 156/643.1, 659.11; 216/65

[56] References Cited

U.S. PATENT DOCUMENTS

| | | | |
|---|---|---|---|
| 4,161,952 | 7/1979 | Kinney et al. | 128/786 |
| 4,291,707 | 9/1981 | Heilman et al. | 128/784 |
| 4,934,049 | 6/1990 | Kiekhafer et al. | 29/883 |
| 4,971,070 | 11/1990 | Holleman et al. | 128/784 |
| 4,978,830 | 12/1990 | Millerick et al. | 219/121.67 |
| 5,099,101 | 3/1992 | Millerick et al. | 219/121.82 |
| 5,216,808 | 6/1993 | Martus et al. | 29/889.1 |
| 5,226,260 | 7/1993 | Mar et al. | 51/319 |

OTHER PUBLICATIONS

"Innovative Laser Systems for Ultraviolet Laser–Based Micromachining", Jerry Martyniuk, et al., *Medical Device & Diagnostic Industry*, pp. 110–121 Oct. 1994.

"Laser Ablation of Organic Polymers: Microscopic Models for Photochemical and Thermal Processes", Barbara J. Garrison, et al., *J. Appl. Phys.*, 57(8), pp. 2909–2914, 15 Apr. 1985.

"Infrared Laser Ablation of Polymers", Robert F. Cozzens, et al., *Polymer Engineering and Science*, vol. 18, No. 11, pp. 900–904, Aug. 1978.

"Pulsed Laser Stripping of Polyurethane–Coated Wires: A Comparison of KrF and $CO_2$ Lasers", James H. Brannon, et al, *J. Appl. Phys.* 70(7), pp. 3881–3886, 1 Oct. 1991.

"High–Resolution Ablation of Amorphous Polymers Using $CO_2$ Laser Irradiation", Mark F. Sonnenschein, et al, *Appl. Phys. Lett.* 57(5), pp. 425–427, 30 Jul. 1990.

Advertisement from Potomac in *Medical Plastics and Biomaterials*, pp. 17, Fall 1994.

Internet E–Mail Message "Microelectrode Arrays".

*Primary Examiner*—Kathleen Duda
*Attorney, Agent, or Firm*—Steven M. Mitchell; M. Elizabeth Bush; Mark J. Meltzer

[57] ABSTRACT

A method for the automated manufacture of defibrillation lead electrodes is disclosed. A metallic defibrillation electrode coil is first embedded in silicone rubber. The location of the coil is mapped using a machine vision system and then a $CO_2$ laser is used to ablate the silicone overlying the coil to expose a controlled portion of the coil while leaving the remainder securely embedded in the silicone. The power density of the laser is below that which would affect the surface or bulk properties of the coil.

12 Claims, 4 Drawing Sheets

METHOD FOR MANUFACTURING IMPLANTABLE CARDIAC DEFIBRILLATION ELECTRODES USING A LASER BEAM MATERIAL REMOVAL PROCESS

This is a continuation of application Ser. No. 08/291,259, filed on Aug. 16, 1994 U.S. Pat. No. 5,580,699.

FIELD OF THE INVENTION

This invention relates to medical electrical stimulation electrodes in general and to a method for manufacturing implantable defibrillation electrodes in particular.

BACKGROUND OF THE INVENTION

It is well known that cardiac arrhythmias may be controlled with devices such as implantable defibrillators. Past electrodes which deliver defibrillation therapy have been constructed of metal mesh adhered to a silicone rubber backing as disclosed in Heilman et al. in U.S. Pat. No. 4,291,707 or have been constructed of metal electrode coils adhesively bonded to a silicone rubber backing as disclosed in Holleman et al. in U.S. Pat. No. 4,971,070.

These electrodes have been manufactured using various techniques. In the case of the Heilman electrode, the electrode metal mesh is either stitched onto the rubber sheeting, or sandwiched between two layers of silicone rubber sheeting, one solid, and the other with open windows to allow for current distribution. The problem with these manufacturing processes is that the electrode is not firmly attached to the silicone rubber sheeting in all areas. Thus, tissue will have a tendency to grow into the electrode mesh and separate the electrode from the backing. If the need arises for explanting the electrode, complications arise due to the difficulty in separating the electrode from the ingrown tissue. In addition, the manufacturing methods are somewhat cumbersome to utilize.

In the case of the Holleman electrode, the electrode coils are adhesively bonded to the silicone sheeting, either with or without a central silicone core inserted into the coil. This technique involves an adhesive bonding step which must be carefully administered in order to ensure adequate bonding to all the surfaces. In addition, by using an adhesive, another material, which must be biocompatible, is added to the device thus complicating matters.

In U.S. Pat. No. 5,226,260 to Mar et al., a metal is completely embedded in silicone, using a molding operation; then, a jet of abrasive material is directed at the encapsulated metal to expose a portion of it to act as an electrode, leaving an unexposed portion firmly embedded in elastomeric material. The process of blasting the silicone surface layer with abrasive material to expose the metal is time consuming, difficult to control, and done by hand, making it very expensive. This is especially true when the metal of the electrode is of a complex geometry, having tiny coils or a mesh pattern, or when the thickness of silicone encapsulation varies as it usually does when compression molding is used to encapsulate coils.

It is therefore an object of the present invention to provide a method for manufacturing defibrillation electrodes using an automated material removal process.

SUMMARY OF THE INVENTION

This invention is directed to a new electrode fabrication technique which allows for the electrode material to be affixed to the polymeric backing in a simple, reliable manner. The process can selectively remove some materials without damaging others. In this process the electrode material is first completely embedded in a polymer such as silicone rubber, polyurethane, a fluoropolymer, or carbon loaded silicone rubber, during a molding process. Then, selected amounts of electrode material are exposed by using the material removal process of this invention.

In a preferred process, the material removal is accomplished by using a $CO_2$ laser beam at a low enough power density to remove the rubber without changing the surface or the bulk properties of the metal or otherwise damaging the electrode material. The amount of material removed and the removal rate can be controlled by a machine vision system with pattern recognition which maps coil locations for the laser beam ablation. The microprocessor based integrated system translates visual patterns into computer numerical control (CNC) commands for laser beam direction. The system may be capable of processing multiple electrode configurations.

To make electrodes with metal coils partially embedded in silicone rubber, the machine-vision and pattern recognition package maps the electrode, then a laser ablates the silicone off the coil peaks. By selective partial removal of rubber from the electrode, adhesion can be maintained between the silicone rubber backing and the entire electrode surface at all points of electrode/rubber contact. This helps to prevent delamination of the electrode from the silicone, and limits the amount of tissue ingrowth. With less tissue ingrowth into the electrode material, the defibrillation lead is easier to explant at a later time.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1:
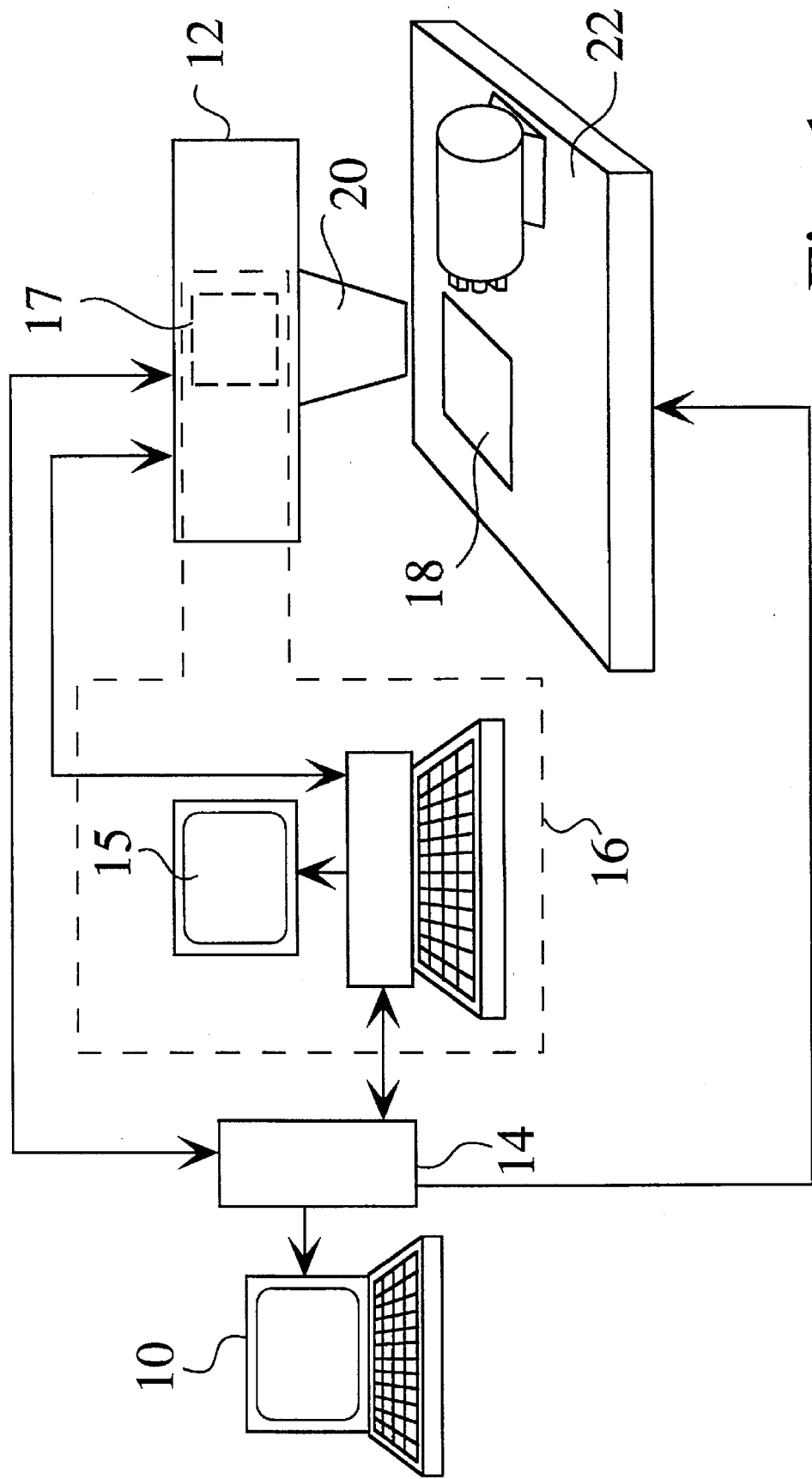
FIG. 1 shows a diagrammatic, plan view of the equipment used and the setup for practice of the material removal process.

FIG. 1 shows a plan view of the equipment used and the setup for the material removal process of the invention. A motion controller 14 connects an industrial PC 10 to a $CO_2$ laser 12 and to a vision system 16 that has the capability of resolving planar dimensions and measuring depth. The vision system contains a central processing unit (CPU) 15 and a camera with microscopic optics 17. The motion control interface may be installed into the PC chassis.

Figure 2:
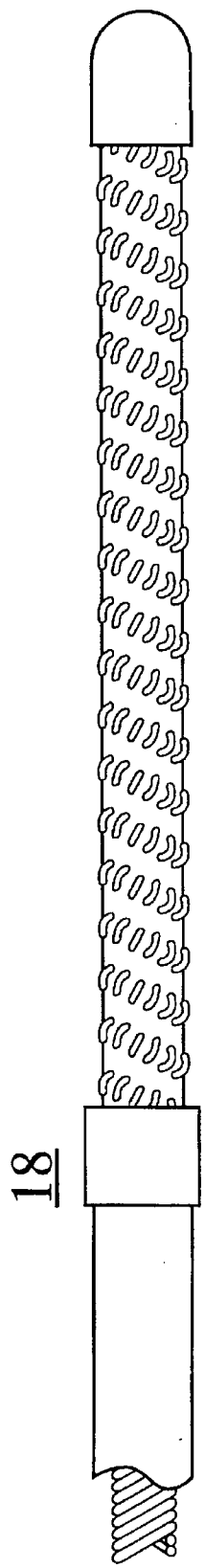
FIG. 2 shows a cylindrical electrode made by the material removal process.

The $CO_2$ laser 12 produces a laser beam which is focused on a workpiece 18 which is supported in a retaining fixture 22. To control the location of the laser beam on the workpiece 18, the laser may be moved using a galvanometer beam positioner 20; or the workpiece may be moved by moving the retaining fixture 22 which may be an x-y table or a rotating chuck; or both may be moved. For example, the cylindrical workpiece shown in FIG. 2, may be a "Flexible Defibrillation Electrode of Improved Construction", U.S. Pat. No. 5,439,485 to Mar et al., which is assigned to the assignee of the present application and is incorporated herein by reference. As shown in FIG. 2, cylindrical translucent or transparent polymeric material encapsulates metal wire in the form of at least one coil helically wound about the same axis as the major axis of the cylindrical polymeric material. The workpiece may be rotated about its long axis while the laser moves back and forth along the long axis of the workpiece. In this way, the laser beam is used to remove polymeric material from the surface of a portion of workpiece 18 and thereby reduce the outer diameter of that portion to less than its initial outer diameter, thereby exposing a portion of the metal wire.

Figure 3:
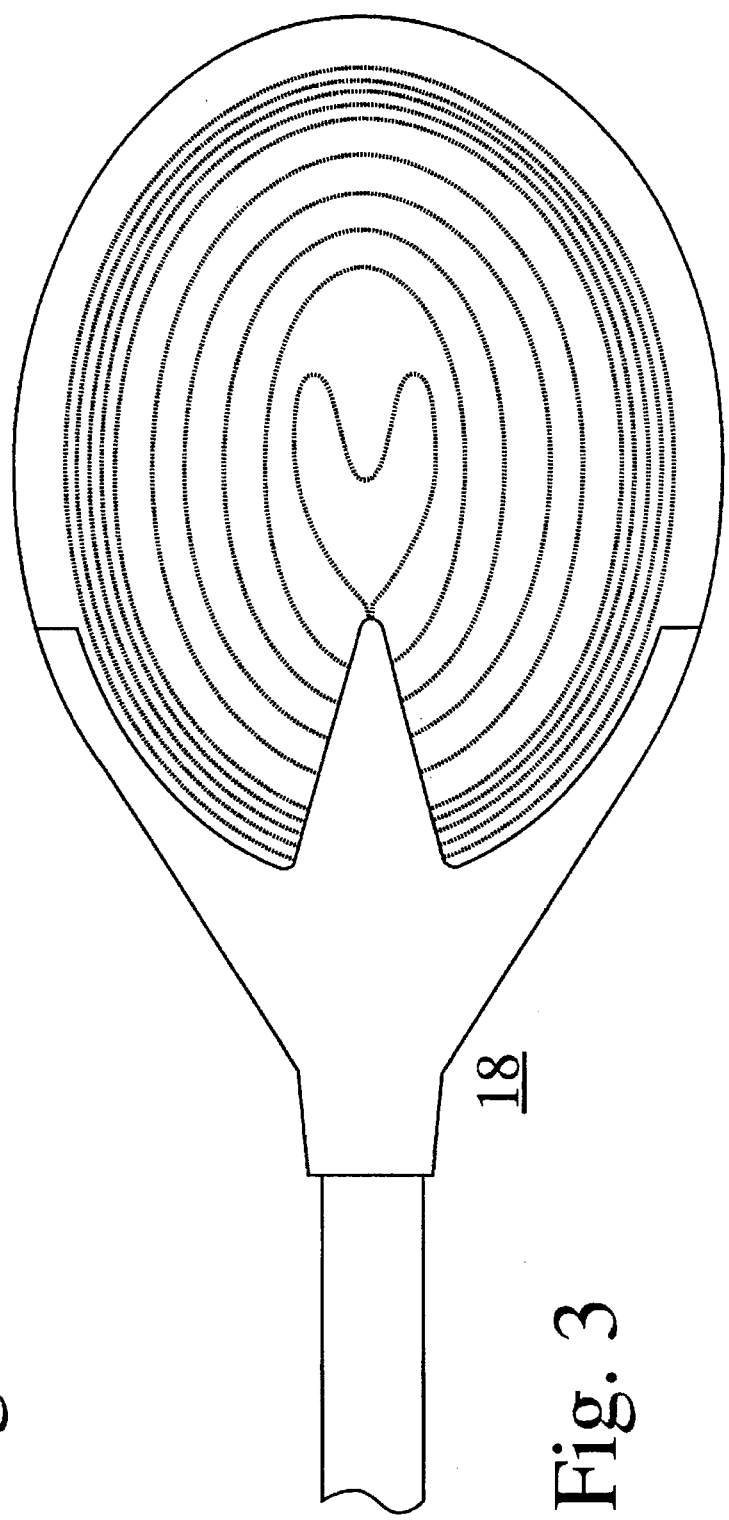
FIG. 3 shows a planar, or "patch", electrode made by the material removal process.

FIG. 3 shows a planar, or "patch", electrode, which can be manufactured by moving either the beam positioner 20 or the workpiece 18. In general, the advantage of moving the laser is speed, while the advantage of moving the workpiece is that it is cheaper and quicker to implement. A vacuum table may be used to hold the planar workpiece 18.

In the configurations of both FIG. 2 and FIG. 3, the metal coils may be tiny in size, on the order of 0.05 to 0.1 mm wire diameter, and 0.1 to 0.5 mm outer coil diameter. The electrode of FIG. 2 may alternatively be made from round or flat wire instead of tiny coils; the electrode of FIG. 3 may alternatively be made from larger coils or from wire mesh.

An inert shielding gas such as argon, nitrogen, or helium may be used to prevent the formation of undesired byproducts of the laser ablation and prevent laser lens contamination. Alternatively, a vacuum system may be used to draw the gaseous byproducts away from the workpiece.

In the above configurations, when a $CO_2$ laser beam strikes the surface of a polymer or metal, the heating energy available is equal to $(1-R) \times E_B$, where R is the reflectivity and $E_B$ is the beam energy. Reflectivity is defined as the ratio of the radiant energy reflected from a surface to the radiant energy striking the surface. At lower power densities, most of the beam energy is reflected. If the power density is high enough, the heating energy is sufficient to cause a photothermal reaction, such as melting or vaporization. It is believed that this phase change at the surface reduces the reflectivity, allowing more of the beam energy to be absorbed into the material. When the power density is increased from a point wherein most of the beam energy is reflected, to power density wherein most is absorbed, the beam is "coupled" with the material; this transition is very abrupt.

The present invention utilizes the difference between the power density required to couple a laser beam to a polymer and to a metal. It is possible to vaporize silicone with a beam power density on the order of $10^5$ watts/square inch which is well below the power density required to couple a beam to and melt platinum ($\sim 10^7$ watts/square inch). Platinum heating is negligible at this power density. The $CO_2$ laser is used due to its ability to couple with polymers such as silicone. Alternatively, a CO laser may be used. However, a YAG laser could not be used effectively for this process because silicone is more transparent to YAG laser wavelengths (about 1.06 μmeters).

Another difference in the behavior of silicone and platinum toward laser energy is a result of their differing thermal conductivities. Metals are generally more thermally conductive than polymers, and tend to conduct the heat away, whereas polymers hold the heat locally, allowing a clean cut to be made.

Due to variation in the location of coils inherent in the molding process, a machine vision system 16 with pattern recognition is used to map coil locations and guide the laser beam to desired ablution sites. The microprocessor based integrated system 16 has the ability to translate visual patterns into CNC commands for laser beam direction. The system has the ability to process multiple electrode configurations, based on configuration specific fixturing.

The machine vision and pattern recognition system 16 maps the electrodes, recognizing the location of metal peaks beneath the surface of the optically transparent or translucent polymer, then a laser ablates the polymer off the metal peaks. Variation in coil depth can be accommodated by optimizing beam parameters, or by using a machine vision system capable of measuring coil depth based on relative size or relative brightness.

The system may be programmed to recognize and ablate individual peaks, or may process a strip of the workpiece at a time. The vision system 16 may work in real time, identifying each desired ablation site immediately prior to laser ablation; this technique may be especially useful when using optically opaque polymers to encapsulate the metal. As a alternative method for using opaque materials, such as carbon loaded silicone rubber, a laser beam may be used to remove some of the material from the surface, thereby exposing peaks of the metal wire; then, a machine vision system 16 may be used to map the locations of the exposed metal wire peaks; lastly, the laser beam is used to remove an additional amount of material as determined by the vision system mapping, thereby exposing an additional amount of the metal wire.

The motion controller 14 coordinates laser and movement timing in order to prevent acceleration and deceleration variation in the ablation sites. This is a function of the pulse repetition rate (frequency) and pulse duration with table movement. In the preferred method, prior to turning on the laser beam, the laser or workpiece is accelerated to a constant velocity at which the ablation will take place; following ablation, the beam is turned off, then the laser or workpiece is decelerated to zero velocity.

Preferably, a beam analyzer (not shown) is used to tightly hold the system power and other parameters in order to lase correctly. The fixturing 22 must prevent the workpiece and the rest of the system from vibrating, since any vibration may introduce errors in depth and location of ablation.

Following the laser ablation of the silicone rubber, the workpiece is removed from the retaining fixture, and a cleaning process may be used to remove ablation byproducts from the surface. Alternatively, such a cleaning process could be minimized by performing the laser ablation in a vacuum, thereby impeding deposition of byproducts onto the surface. Any of the following three cleaning methods can be used to remove byproducts from the surface:

1. Use a low pressure jet of abrasive material such as sodium bicarbonate to remove the ablation byproducts, followed by three ultrasonic cleanings in isopropyl alcohol for seven to ten minutes each.

2. Use a solvent such as heptane to remove the ablation byproducts, followed by three ultrasonic cleanings in isopropyl alcohol for seven to ten minutes each.

3. Use a surfactant such as Ivory soap to remove the ablation byproducts, followed by three ultrasonic cleanings in isopropyl alcohol for seven to ten minutes each.

Because it is fully automated, this laser ablation process decreases throughput times and operator involvement. The system can perform 100% machine-vision inspection after completion of laser ablation. Furthermore, using a laser allows tight process control of silicone removal location and depth.

Figure 5:
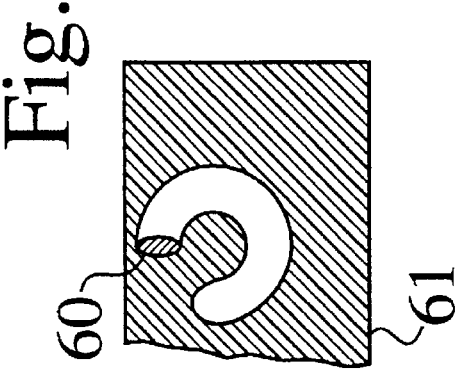
FIG. 5 is an end elevational view, partly in cross section, of FIG. 4.
Figure 4:
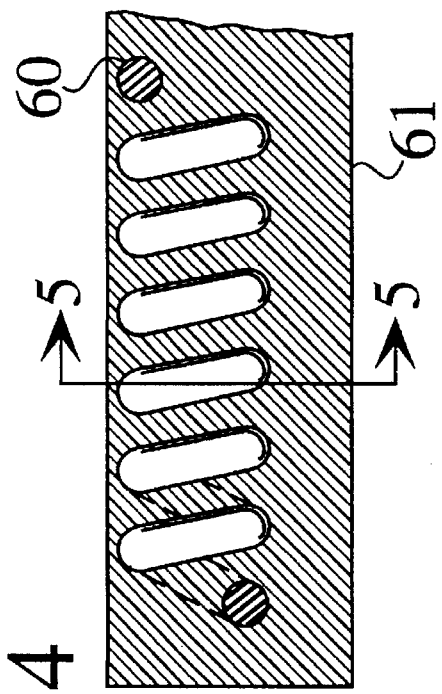
FIG. 4 shows an elevational view, partly in cross section, of a defibrillation electrode coil after it has been completely embedded in silicone rubber.

FIGS. 4 and 5 show a space-wound defibrillation coil electrode after it has been completely embedded in a polymeric material such as silicone rubber. The coil 60 is completely embedded in the rubber 61 (or other polymeric material), from the compression molding process, and may be made, for example, of platinum, or a platinum bearing alloy such as an alloy of 90% platinum and 10% iridium by weight. Note that due to the space-wound structure of the coil, the interior and exterior portions of the coil are adhered to the silicone rubber backing.

Figure 7:
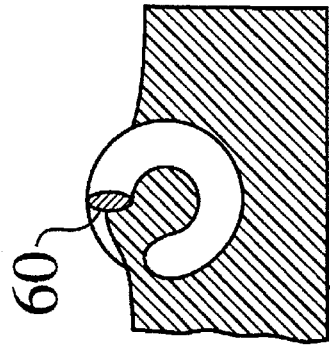
FIG. 7 is an end elevational view, taken partly in section, of FIG. 6.
Figure 6:
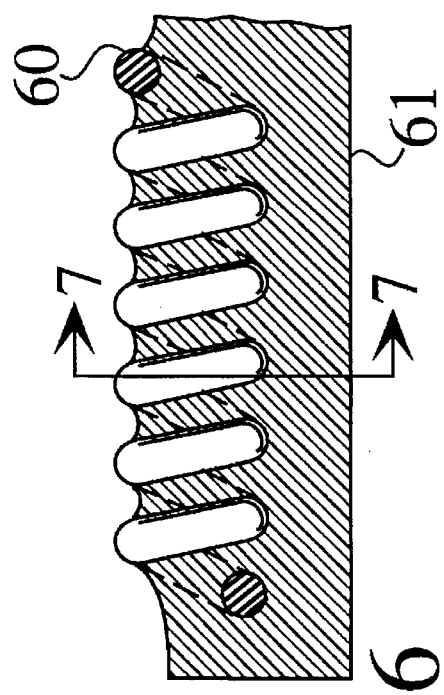
FIG. 6 shows an elevational view, partly in cross section, of the same portion of defibrillation electrode coil of FIG. 4 after the silicone backing has been partially removed.

FIGS. 6 and 7 show the space-wound defibrillation coil electrode after the removal process. The top portion of the rubber backing 61 has been removed from the ablation process to partially expose the coil 60. Note that the bottom portion of the coil is still completely embedded in the silicone rubber backing. This ensures excellent adhesion to the silicone for the life of the device. The amount of coil embedded in rubber and the amount of coil exposed can be varied between the conditions shown in FIG. 4 and FIG. 6, thus allowing excellent control over the electrode/rubber adhesion and amount of surface area for current delivery.

Figure 8:
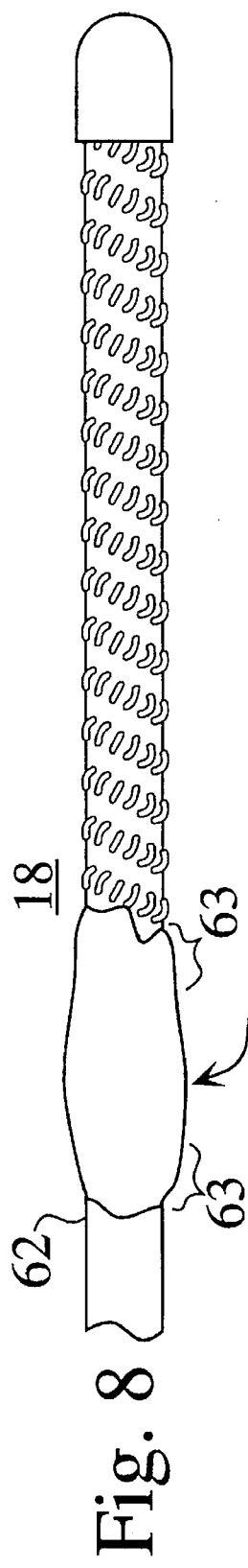
FIGS. 8 and 9 show excess rubber that is removed from a molded joint.
Figure 9:
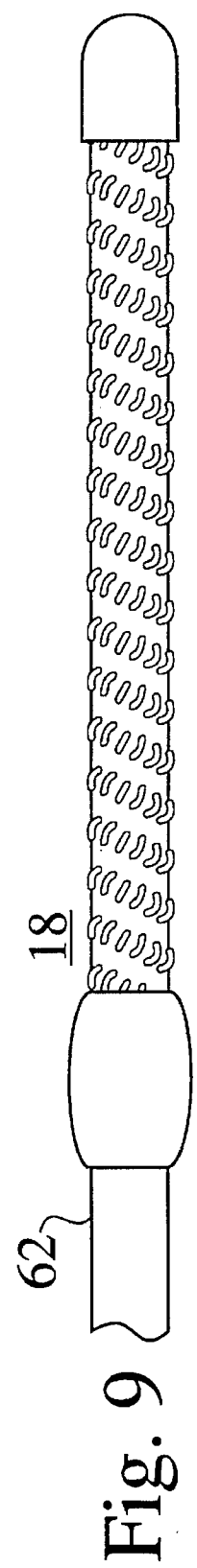

FIGS. 8 and 9 demonstrate how this process can be used in rework operations. In FIG. 8, there is excess rubber 63 resulting from molding the joint 64 connecting the electrode to the lead body insulation 62. In FIG. 9, the excess rubber has been removed using the laser with vision system and material removal method of the present invention.

Figure 10:
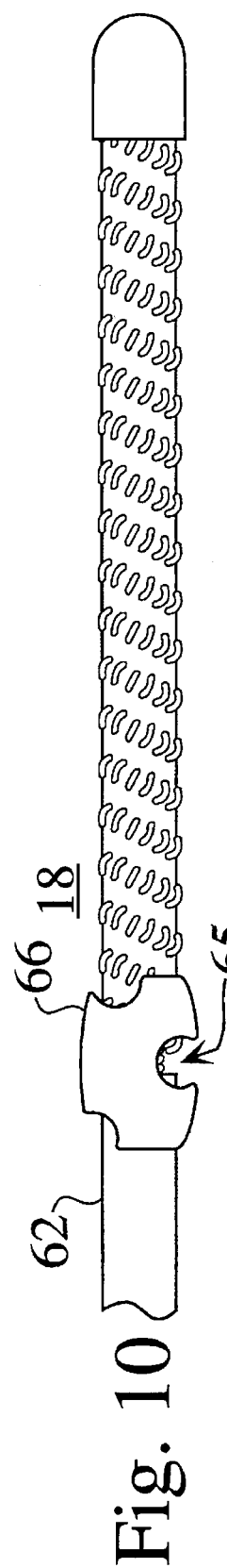
FIGS. 10 and 11 show an unsuccessfully molded joint that is laser ablated to prepare for a remolding operation.
Figure 11:
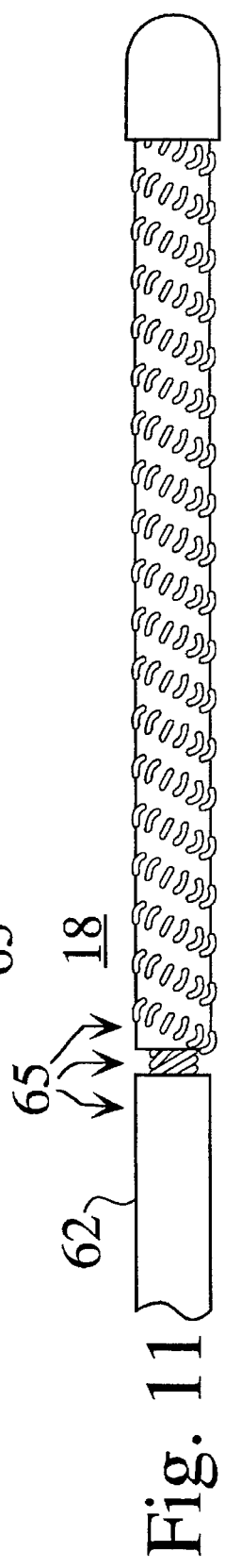

FIG. 10 illustrates a case where the molding operation was unsuccessful but did not damage the underlying components 65. In FIG. 11, the molded material 66 has been removed using the laser with vision system and material removal method of the present invention, to prepare for a remolding operation.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. An automated method of manufacturing an implantable cardiac electrode comprising the steps of:

(a) encapsulating a metal conductor in a polymeric material;

(b) directing a laser beam at said polymeric material; and (c) photothermally vaporizing a portion of said polymeric material using said laser beam to expose a portion of said metal conductor whereby an unexposed portion of said metal conductor remains embedded in said polymeric material, thereby forming a partially embedded metal conductor.

2. The method of claim 1 wherein said step (b) of directing a laser beam at said polymeric material comprises providing a $CO_2$ laser beam.

3. The method of claim 1 wherein said step (b) of directing a laser beam at said polymeric material comprises positioning said metal conductor encapsulated in said polymeric material using an x–y table.

4. The method of claim 1 wherein said step (a) of encapsulating a metal conductor in a polymeric material comprises providing silicone rubber as the polymeric material.

5. The method of claim 1 wherein said step (a) of encapsulating a metal conductor comprises providing a platinum bearing alloy as the metal conductor.

6. The method of claim 1 wherein said step (a) of encapsulating a metal conductor further comprises the step of providing a coiled metal wire as said metal conductor.

7. The method of claim 1 wherein said step (a) of encapsulating a metal conductor in a polymeric material comprises compression molding said polymeric material around said metal conductor.

8. The method of claim 1, further comprising the steps of:

(d) providing a lead body insulation having a proximal end and a distal end;

(e) positioning said distal end near a portion of said partially embedded metal conductor;

(f) molding rubber over said portion of said partially embedded metal conductor and over said distal end of said lead body insulation to form a joint with said lead body insulation; and (g) removing any excess rubber after step (f) by photothermally vaporizing said excess rubber with said laser beam.

9. The method of claim 1, further comprising the steps of:

(d) providing a lead body insulation;

(e) molding rubber over a portion of said partially embedded metal conductor and over a portion of said lead body insulation to form a joint with said lead body insulation;

(f) reworking the joint by removing at least a portion of said rubber by photothermally vaporizing said rubber with said laser beam; and (g) repeating step (e).

10. An automated method of manufacturing a cylindrical implantable medical lead comprising the steps of:

(a) encapsulating a metal wire in a cylindrical translucent or transparent polymeric material having an initial outer diameter; and (b) directing a laser beam at a portion of said polymeric material to photothermally remove some of said polymeric material from the surface of said portion and thereby reduce the outer diameter of said portion to less than said initial outer diameter, thereby exposing a portion of said metal wire.

11. The method of claim 10, wherein said step (a) of encapsulating a metal wire comprises providing as the metal wire at least one coil helically wound about the same axis as the major axis of said cylindrical translucent or transparent polymeric material.

12. An automated method of manufacturing an implantable medical lead comprising the steps of:

(a) encapsulating a metal wire in an opaque material, said metal wire being coiled to provide a plurality of peaks and troughs; and (b) directing a laser beam at said material to photothermally remove some of said material from the surface of said material and thereby expose at least some of said peaks of said metal wire.

* * * * *